(12) United States Patent
Thorner (10) Patent No.: US 9,763,919 B2
(45) Date of Patent: Sep. 19, 2017

(54) DETECTING AND TREATING GROWTH HORMONE DEFICIENCY

(71) Applicant: Ammonett Pharma LLC, Midlothian, VA (US)

(72) Inventor: Michael Oliver Thorner, Charlottesville, VA (US)

(73) Assignee: AMMONETT PHARMA, LLC, Midlothian, VA (US)

( * ) Notice: Subject to any disclaimer, the term of this patent is extended or adjusted under 35 U.S.C. 154(b) by 0 days.

(21) Appl. No.: 15/271,542

(22) Filed: Sep. 21, 2016

(65) Prior Publication Data

US 2017/0079961 A1 Mar. 23, 2017

Related U.S. Application Data

(60) Provisional application No. 62/289,221, filed on Jan. 30, 2016, provisional application No. 62/221,191, filed on Sep. 21, 2015.

(51) Int. Cl.
*A61K 31/435* (2006.01)
*G01N 33/74* (2006.01)

(52) U.S. Cl.
CPC .......... *A61K 31/435* (2013.01); *G01N 33/74* (2013.01); *G01N 2333/61* (2013.01); *G01N 2333/65* (2013.01)

(58) Field of Classification Search
CPC ...... A61K 31/435; A61K 9/20; A61K 9/0053; G01N 33/74; G01N 2333/65; G01N 2333/61
See application file for complete search history.

(56) References Cited

U.S. PATENT DOCUMENTS

| | | | |
|---|---|---|---|
| 5,756,507 | A | 5/1998 | Goulet et al. |
| 6,861,409 | B2 | 3/2005 | Martinez et al. |
| 8,192,719 | B2 | 6/2012 | Larsen |
| 2003/0225096 | A1 | 12/2003 | Hakkinen |
| 2004/0229823 | A1 | 11/2004 | Martinez et al. |
| 2006/0142264 | A1 | 6/2006 | Funamizu et al. |
| 2007/0037861 | A1* | 2/2007 | Cutfield ............... A61K 31/192 514/356 |
| 2010/0120661 | A1 | 5/2010 | Campbell et al. |
| 2015/0119327 | A1* | 4/2015 | Muotri ................... A61K 31/13 514/8.6 |

OTHER PUBLICATIONS

Gasco, Valentina et al., Acylated ghrelin as a provocative test for the diagnosis of GH deficiency in adults, European Journal of Endocrinology (2013) 168 23-30.

Kelly, Andrea, et al., Age-Based Reference Ranges for Annual Height Velocity in US Children, J Clin Endocrinol Metab, Jun. 2014, 99(6):2104-2112.

Murray, P. G., et al., Controversies in the diagnosis and management of growth hormone deficiency in childhood and adolescence, Arch Dis Child 2015, 0, 1-5.

Chapman, Ian M. et al., Oral Administration of Growth Hormone (GH) Releasing Peptide-Mimetic MK-677 Stimulates the GH/Insulin-Like Growth Factor-I Axis in Selected GH-Deficient Adults, Journal of Clinical Endocrinology and Metabolism 1997, vol. 82 (10), 3455-61.

Tanner, J. M., et al., Clinical longitudinal standards for height and height velocity for North American children, J. Pediatrics 1985, 107(3), 317-29.

Codner, Ethel et al., Effects of oral administration of ibutamoren mesylate, a nonpeptide growth hormone secretagogue, on the growth hormone-insulin-like growth factor I axis in growth hormone-deficient children, Clincal Pharmacology & Therapeutics Jul. 2001, 91-98.

Smith, Roy G., et al., Peptidomimetic Regulation of Growth Hormone Secretion, Endocrine Reviews 1997, 18(5): 621-645.

Severs, Evelien F., et al., Growth, Growth Hormone (GH)-Binding Protein, and GH Receptors Are Differentially Regulated by Peak and Trough Components of the GH Secretory Pattern in the Rat, Endocrinology 1996, 137(3), 1013-18.

Ghigo, Ezio, et al., Biologic Activities of Growth Hormone Secretagogues in Humans, Endocrine 2001, 14(1), 87-93.

Alatzoglou, Kyriaki S., et al., Isolated Growth Hormone Deficiency (GHD) in Childhood and Adolescence: Recent Advances, Endocrine Reviews, Jun. 2014, 35(3):378-432.

Garcia, J. M., et al., Macimorelin (AEZS-130)-Stimulated Growth Hormone (GH) Test: Validation of a Novel Oral Stimulation Test for the Diagnosis of Adult GH Deficiency, J Clin Endocrinol Metab, Jun. 2013, 98(6):2422-2429.

Nargund, Ravi P., et al., Peptidomimetic Growth Hormone Secretagogues. Design Considerations and Therapeutic Potential, Journal of Medicinal Chemistry, 1998, 41(17), 3103-27.

Marianne Andersen, The robustness of diagnostic tests for GH deficiency in adults, Growth Hormone & IGF Research 2015, 25, 108-14.

Shah A. et al., Hazards of pharmacological tests of growth hormone secretion in childhood, BMJ 1992, 304, 173-4.

PCT/US16/52800 Written Opinion, mailed Dec. 15, 2016.

* cited by examiner

*Primary Examiner* — Sudhakar Katakam
(74) *Attorney, Agent, or Firm* — Vance Intellectual Property, PC (57) ABSTRACT

Described herein is a new oral method for using MK-0677 for detecting growth hormone (GH) deficiency (GHD). Also described is a method of treating growth hormone (GH) deficiency (GHD) in children with a functional hypothalamic-pituitary GH axis.

20 Claims, 5 Drawing Sheets

DETECTING AND TREATING GROWTH HORMONE DEFICIENCY

FIELD OF THE INVENTION

The present invention relates a new oral method for using MK-0677 for detecting growth hormone (GH) deficiency (GHD) in patients. The present invention also relates to a method of treating growth hormone (GH) deficiency (GHD) in children with a functional hypothalamic-pituitary GH axis.

BACKGROUND OF THE INVENTION

Growth hormone (GH) is an anabolic anterior pituitary hormone that stimulates cellular proliferation and differentiation through the synergistic action of GH and insulin-like growth factor-1 (IGF-1). In vivo, the biosynthesis and secretion of GH is regulated by the balance of growth hormone releasing hormone (GHRH) and somatostatin (SST). GH secretion is also subject to feedback mechanisms of control at both the hypothalamus and the pituitary. Secretion of GH is critical to normal skeletal growth during childhood, with maximum secretion occurring during puberty. Deficient secretion of GH in children results in short stature, retarded height velocity, and delayed bone maturation.

A subset of the 3% of children with short stature are growth hormone deficient (GHD), with a prevalence of approximately 1 child per 3700 to 4000. Currently the diagnosis of GH deficiency (GHD) is made in children first based on their slow growth and short stature and delay in bone age. The diagnosis is then confirmed by performing a stimulation test of GH secretion. These standard stimulation tests include insulin induced hypoglycemia, infusion of aginine, glucagon administration subcutaneously, or oral administration of levo-dopa or clonidine. Although insulin induced hypoglycemia is considered the most reliable it requires that the child is supervised by a physician for the two hours that the test takes; in addition adverse effects that include two reported deaths have occurred during insulin induced hypoglycemia (REFS). For these reasons insulin induced hypoglycemia is not used by pediatric endocrinologists and the other tests are used. The glucagon test is probably the most reliable but, to further enhance reliability, two tests are usually performed. Recently growth hormone secretagogue receptor (GHS-R) agonists have been used and they have the advantage of being reliable but the peak GH response defining GH deficiency is poorly characterized. It would be beneficial to develop a GHD test that is easier to use, safer, and/or more reliable than the current tests.

Ibutamoren mesylate (MK-0677) was developed at Merck Research Laboratories (Merck) as a specific orally active growth hormone secretagogue. Merck conducted a phase IIb study of children with variable degrees of short stature and growth hormone deficiency (GHD) in 1996-98. They treated the children with either placebo or the growth hormone secretagogue receptor agonist MK-0677 or with rhGH (recombinant hormone growth hormone). MK-0677 mimics the effect of the now recognized natural ligand for the growth hormone secretagogue receptor, which is the hormone ghrelin. The rationale was to determine whether oral therapy with MK0677 would accelerate growth effectively in children with short stature.

In the Phase IIb study, 24 children were treated with 0.8 mg/kg/d MK-0677. These children had a baseline growth rate of 3.4±1.7 cm/y (centimeter/year), which increased to 6.8±2.0 cm/y at 6 months with a significant change in growth rate of 3.4±2.1 cm/y. This can also be expressed as a height velocity standard deviation (SD) (or standard deviations—also SD) at baseline of 0.4±2.1 and 3.5±2.0 at 6 months. In contrast a group of 22 children treated with placebo had a baseline growth rate of 4.2±1.8 cm/y and 4.6±1.4 cm/year at 6 months with a statistically insignificant change in growth rate of 0.4±2.3 cm/y. Change in height velocity SD for chronological age was 0.4±2.1 for placebo and 3.5±2.0 for treatment with MK-0677 after 6 months at a dose of 0.8 mg/kg/d. Twenty of the 22 placebo-treated children were then treated with standard Growth Hormone (GH) treatment (daily subcutaneous injection of rhGH, 0.043 mg/kg/day). These showed an increase in their height velocity SD score for chronological age from 0.3±2.2 at baseline (i.e., 6 months of placebo treatment) to 7.6±5.6. Since the increase in height velocity SD was twice as high for GH than for MK-0677 treatment, the project was discontinued as MK-0677 was deemed less effective and not competitive with the standard GH therapy.

GHD leading to short stature (−2 SD height for chronological age) in children is a disorder found worldwide. Treatment of growth hormone deficient children having short stature lasts typically for many years from diagnosis in childhood to reaching final height. Results obtained from 6 months assessment of treatment in newly-diagnosed children can be widely variable due to the differences in underlying etiology of the GH deficiency, and patterns and rates of catch-up growth on start of treatment. Typically treatment for 1 year or longer is necessary to establish a new growth trajectory on treatment. Thereafter, treatment is often required for 10 years or more, to reach an optimal adult height in these children. Children with GHD are usually treated by daily subcutaneous injections of GH, which can be painful, inconvenient, and cause distress in some, especially younger, children. It would be beneficial in terms of ease of treatment, patient convenience, and long-term adherence to develop non-injection based therapies, e.g., a once-per-day oral treatment, if such therapies could be shown to have similar efficacy to GH in some groups of GHD patients.

SUMMARY OF THE INVENTION

In an aspect, the present invention provides a novel method of testing for GHD.

In an aspect, the present invention provides a novel method of treating GHD in children with adequate GH secretion potential.

In an aspect, the present invention provides a novel method of treating GHD in children with equivalent growth potential compared to treatment with rhGH.

In another aspect, the present invention provides novel method of testing and identifying patients for adequate GH secretion potential.

In another aspect, the present invention provides novel method of testing and identifying patients with equivalent growth potential compared to treatment with rhGH.

These and other aspects, which will become apparent during the following detailed description, have been achieved by the inventors' discovery that MK-0677 can be used to test for GHD as well as treat certain subpopulations of children with GHD.

BRIEF DESCRIPTION OF DRAWINGS

FIG. 1 shows the height velocity after GH (0.3 mg/kg/week; ~0.043 mg/kg/day sc injections) (N=20) and MK-0677 (0.8 mg/kg/day) once daily oral treatment (N=24)

for 6 months for patients. The response to rhGH in the overall patient group is superior to MK-0677.

FIG. 3A and FIG. 3B show that the height velocity after MK-0677 treatment for 6 months is equal to GH treatment in the EQUAL patient group.

DETAILED DESCRIPTION OF PREFERRED ASPECTS

In an aspect of the present invention, a novel test has been developed with two objectives:
(i.) To provide a simple, reliable, and easily conducted test for establishing GHD that will be able to performed by a nurse practitioner rather than requiring a physician; and,
(ii.) To identify GHD children who will have an equivalent increase in growth velocity to once daily oral MK-0677 therapy as they would to daily subcutaneous (sc) recombinant GH (rhGH) injections.

In the MK-0677 Phase IIb study described above, all GHD children had been grouped together by Merck. However, analysis of the characteristics showed that these patients exhibited wide variation in their severity of GHD and height velocities. When these data were reanalyzed taking the severity of GHD as well as their ability to respond with GH response to a MK-0677 challenge into account, we discovered that the growth responses of a subpopulation children to oral treatment with MK-0677 was surprisingly similar to their responses to injections of GH (i.e., rhGH). The children who were severely GH deficient as identified by their inability to increase their peak GH to >5 µg/L and/or having a baseline IGF-I of <30 µg/L had an increase in height velocity in response to exogenous GH therapy; whereas those treated with MK-0677 were less responsive. However the children in the equivalent growth potential group compared to rhGH (acute peak GH response of ≥5 µg/L to a single dose of MK-0677 and a baseline serum IGF-I of >30 µg/L)(EQUAL patient group) responded with equivalent growth response to both exogenous GH injections and a daily oral dose of MK-0677. By avoiding injections, once daily oral administration of MK-0677 would have many advantages as a method of treatment compared to GH injections and would allow for much easier and greater patient adherence. Since adherence is a critical component of any treatment, the ease of treatment with MK-0677 versus GH (oral versus injection) would allow a physician to choose long-term treatment with oral MK-0677 in preference to GH injections given a similar efficacy in terms of height velocity.

Profound GH deficiency is associated with low levels of serum IGF-I. Serum IGF-1 is a biomarker of growth hormone action, and 80% of the circulating serum IGF-1 is produced in the liver. At baseline the relationship between baseline serum IGF-1 and peak response to standard stimulation tests (clonidine, insulin, arginine, glucagon, and L-Dopa) was $r^2$=0.3, while the relationship of baseline serum IGF-1 to peak GH response to MK-0677 was $r^2$=0.7 demonstrating that the MK-0677 test is a better indicator of endogenous growth hormone secretion than the standard tests. Further, depending on which cut off is used for the standard tests, the response to MK-0677 increases. The peak serum GH measured during the MK-0677 challenge test (a single does of MK-0677) is robust. The presence of a peak GH of ≥5 µg/L indicates that the hypothalamic-pituitary GH axis can be stimulated by MK-0677 characterizing the patient as having GH secretion potential. GH deficiency may be associated with profound deficiency, where the hypothalamic-pituitary GH axis is damaged and is unresponsive to MK-0677 administration. Alternatively dysfunction of the hypothalamic-pituitary GH axis may render the patient unable to secrete sufficient GH to sustain normal growth. In such patients the MK-0677 test will determine whether they are fully deficient or if they have insufficient GH secretion and can mount a GH response indicating that the axis is responsive to MK-0677.

In another aspect, the present invention provides a novel method of treating growth hormone deficiency (GHD) in children, comprising: administering a therapeutically effective amount of MK-0677 to a child known to have short stature and adequate GH secretion potential. In another aspect, the child is known to have growth retardation.

In another embodiment, the present invention provides a novel method of treating GHD in children, comprising: administering a therapeutically effective amount of MK-0677 to a child known to have short stature and equivalent growth potential compared to rhGH. In another aspect, the child is known to have growth retardation.

In another aspect, the present invention provides a novel method of treating GHD in children, comprising:
a testing a child for short stature;
b testing for GHD using a theranostic test; and,
c orally administering a therapeutically effective amount of MK-0677 to a child found to have short stature and equivalent growth potential compared to rhGH.

In another aspect, the present invention provides a novel method of treating GHD in children, comprising:
a testing a child known to have short stature for GHD using a theranostic test; and,
b orally administering a therapeutically effective amount of MK-0677 to a child found to have equivalent growth potential compared to rhGH.

In another aspect, the theranostic test, comprises:
(i.) testing for a peak serum GH≥5 µg/L in response to a single oral dose of MK-0677; and,
(ii.) testing for a baseline serum IGF-I of >30 ng/mL.

In another aspect, the theranostic test, further comprises:
(iii.) testing for a peak serum GH of <10 µg/L in response to a standard provocative test.

Alternatively, the testing is for a peak serum GH level of <7 µg/L to a standard provocative test.

In another aspect, pediatric GHD is treated.

In another aspect, mini-tablets, comprising: MK-0677, are orally administered.

In another aspect the number of mini-tablets can be adjusted to allow weight based dosing.

In another aspect, the orally administering, further comprises: administering with the assistance of a device capable of dispensing at least one MK-0677 mini-tablet.

In another aspect, the device is also capable of at least one of the following:
  a reminding a patient or caregiver when medication is to be administered;
  b dispensing the prescribed number of mini-pills;
  c recording the date and time when the mini-pills are dispensed;
  d remotely connecting with a medical practitioner;
  e having the dosage set by a medical practitioner or via approval of the medical practitioner; and,
  f being secure enough to prevent a patient from changing the number of pills dispensed.

In another aspect, the device is capable of: having the dosage remotely (e.g., via a wireless or wired connection to the Internet) set by a medical practitioner or via approval of the medical practitioner.

In some patients, specifically children, the hypothalamic-pituitary growth hormone axis is intact and further stimulation will increase growth. Thus, the present invention also relates to treating indications outside of the standard GHD indications (e.g., pediatric GHD).

In another aspect, the present invention provides a novel method of of treating a pediatric indication, comprising:
  a testing a child for GHD using a theranostic test; and,
  b orally administering a therapeutically effective amount of MK-0677 to a child found to have equivalent growth potential compared to rhGH;
wherein the pediatric indication is selected from:
  (i) infants born small-for-gestational-age who fail to catch up to normal growth curves by age 2;
  (ii) Turner syndrome;
  (iii) SHOX gene deficiency;
  (iv) Noonan syndrome;
  (v) Chronic renal failure; and,
  (vi) Idiopathic short stature;

In another aspect, the present invention provides a novel method of treating GHD in children, comprising:
  (i.) testing a child having short stature (and optionally growth retardation) to determine if he or she has adequate GH secretion potential;
  (ii.) administering a therapeutically effective amount of MK-0677 to the child if found to have adequate GH secretion potential.

In another aspect, the child is tested for adequate GH secretion potential by a method, comprising:
  (i.) testing for a peak serum GH of <10 µg/L in response to a standard provocative test; and,
  (ii.) testing for a peak serum GH≥5 µg/L in response to a single oral dose of MK-0677.

These cut-off values for standard provocative tests are based on commonly accepted current guidelines and depend on the use of well-validated clinical assays. Alternatively, the testing is for a peak peak serum GH level of <7 µg/L to a standard provocative test.

In another aspect, the present invention provides a novel method of treating GHD in children, comprising:
  (i.) testing a child having short stature (and optionally growth retardation) to determine if he or she has equivalent growth potential compared to rhGH;
  (ii.) administering a therapeutically effective amount of MK-0677 to the child if found to have equivalent growth potential compared to rhGH.

In another aspect, the child is tested for equivalent growth potential compared to rhGH by a method, comprising:
  (i.) testing for a peak serum GH≥5 µg/L in response to a single oral dose of MK-0677; and,
  (ii.) testing for a baseline serum IGF-I of >30 µg/L.

These cut-off values are based on commonly accepted current guidelines and depend on the use of well-validated clinical assays.

In another aspect, a method of the present invention, further comprises: testing the child to determine if he or she is prepubertal and proceeding with administering if the child is found to be prepubertal in addition to the above-noted findings.

In another aspect, the method further comprises: testing the child to determine if he or she is peri-pubertal and proceeding with administering if the child is found to be peri-pubertal in addition to the above-noted findings.

In another aspect, the present invention provides a novel theranostic test for determining if a patient will be responsive to therapy with MK-0677, comprising:
  (i.) testing a patient for a peak serum GH≥5 µg/L in response to a single oral dose of MK-0677; and,
  (ii.) testing a patient for a baseline serum IGF-I of >30 ng/mL;
wherein a patient satisfying (i) and (ii) is considered to be responsive to therapy with MK-0677.

In another aspect, the testing for peak serum, comprises:
  a. administering a single, oral dose of MK-0677 to the patient; and,
  b. testing the GH serum levels achieved after administering MK-0677 to determine the patient's peak serum GH level.

In another aspect, the present invention provides a novel theranostic test for determining if a patient will be responsive to therapy with MK-0677, comprising:
  (i.) testing a patient for a peak serum GH≥5 µg/L in response to a single oral dose of MK-0677;
wherein a patient satisfying (i) is considered to be responsive to therapy with MK-0677.

In another aspect, the present invention provides a novel theranostic test for diagnosing growth hormone deficiency, comprising:
  (i.) testing a patient for a peak serum GH≥5 µg/L in response to a single oral dose of MK-0677;
wherein a patient satisfying (i) is considered to be growth hormone deficient.

In another aspect, the present invention provides a novel method of treating growth hormone insufficiency (GHI) in children, comprising: administering a therapeutically effective amount of MK-0677 to a child known to have short stature and adequate GH secretion potential. In another aspect, the child is known to have growth retardation.

In another embodiment, the present invention provides a novel method of treating GHI in children, comprising: administering a therapeutically effective amount of MK-0677 to a child known to have short stature and equivalent growth potential compared to rhGH. In another aspect, the child is known to have growth retardation.

In another aspect, the present invention provides a novel theranostic test for diagnosing GHI, comprising:
  (i.) testing a patient for a peak serum GH≥5 µg/L in response to a single oral dose of MK-0677; and,
  (ii.) testing a patient for a baseline serum IGF-I of >30 ng/mL;
wherein a patient satisfying (i) and (ii) is considered to be growth hormone insufficient.

In another aspect, the present invention provides a novel theranostic test for diagnosing GHI, comprising:
(i.) testing a patient for a peak serum GH≥5 μg/L in response to a single oral dose of MK-0677;
wherein a patient satisfying (i) is considered to be growth hormone insufficient.

In another aspect, the present invention provides a novel method of treating GHI, comprising:
(i.) orally administering once daily mini-tablets, comprising: 2 mg of MK-0677;
wherein MK-0677 administered once daily orally as mini-tablets is equally effective compared to daily recombinant human growth hormone injections in treatment of short stature in children with growth hormone insufficiency who are judged to have equivalent growth potential with MK-0677 therapy as with rhGH. Such children are identified by the finding of a pretreatment serum IGF-I of >30 μg/L and a peak serum growth hormone of >5 μg/L after a single 0.8 mg/kg body weight dose of ibutamoren administered with mini-tablets, comprising: 2 mg MK-0677.

The test for adequate and/or equivalent GH secretion potential is an outpatient test that identifies a population of children who respond to oral MK-0677 therapy as well as to standard daily GH treatment.

In another aspect, the present invention provides MK-0677 for use in therapy.

In another aspect, the present invention provides the use of the present invention for the manufacture of a medicament for the treatment of an indication recited herein.

In another aspect, the present invention provides a novel composition comprising an active action that is MK-0677 for use in the treatment of an indication recited herein.

Patient refers to a human patient, either child or adult. Examples include a child, a prepubertal child, a peripubertal child, and an adult.

In another aspect, the child is known to have growth retardation.

In another aspect, the child is prepubertal.

In another aspect, the child is peripubertal.

Testing for GH: peak GH serum levels of a subject can be measured by using a well known provocative test.

Provocative Test: Provocative tests are well known and include the clonidine test, insulin test, arginine test, glucagon test, and levodopa (L-dopa) test (see Example 4 below). In these tests, the agent of interest is administered to the patient (dosage is typically set based on weight) and sufficient blood samples (e.g., prior to administration and t=15, 30, 60, and 120 minutes post administration) are drawn to determine peak GH secretion. Blood samples can be analyzed for GH using one of the many well known GH assays (e.g., a GH immunoradiometric (IRMA) assay). In the insulin test blood glucose is also measured.

Testing for GH secretion with MK-0677: A single, oral dose of MK-0677 is administered to a patient and sufficient blood samples are taken prior to and after administration (e.g., 15 minutes before and t=0, 30, 60, 90, and 120 minutes after administration) to measure the peak GH secretion. An example of the amount of MK-0677 administered is 0.8 mg/kg. In an aspect, the patient being tested will have fasted overnight (abstinence from all food and drink but water).

Testing for the level of pretreatment serum IGF-I: The level of pretreatment serum IGF-I is the IGF-I level of a patient determined prior to treatment with either exogenous GH or MK-0677.

Child or children: a male or female greater than 4 years of age.

Adult: a male or female whose growth is completed and has fused epiphyses by X-ray based on Grulich and Pyle atlas.

Prepubertal: a child having a bone age of <8 years for female children and <9 years for male children. Bone age can be determined using a well known method such as the atlas matching method of Greulich and Pyle or the point scoring system of Tanner and Whitehouse. Other examples of bone age include <7 for females and <8 for males.

Peripubertal: a child who has started to go through puberty which is assessed clinically by Tanner staging. Tanner stage 1 is prepubertal and anything past that until puberty is complete (Tanner stage 4) is considered peripubertal.

Short Stature: where a child's stature is below the 2.3 percentile (~−2 SD height for chronological age) for his/her chronological age. Other examples include being below the $5^{th}$, $4^{th}$, $3^{rd}$, $2^{nd}$, and $1^{st}$ percentile for his/her chronological age.

Growth Retardation or Slow Height Velocity: a height velocity less than the $25^{th}$ percentile for age and gender, as recorded over at least a 6-month period. Other examples include being below the $24^{rd}$, $23^{rd}$, $22^{nd}$, $21^{st}$, $20^{th}$, $19^{th}$, $18^{th}$, $17^{th}$, $16^{th}$, $15^{th}$, $14^{th}$, $13^{th}$, $12^{th}$, $11^{th}$, $10^{th}$, $9^{th}$, $8^{th}$, $7^{th}$, $6^{th}$, $5^{th}$, $4^{th}$, $3^{rd}$, $2^{nd}$, and $1^{st}$ percentile for age and gender, as recorded over at least a 6-month period.

Adequate GH Secretion Potential: a patient is considered to have adequate GH secretion potential if the patient:
(i.) has a peak GH of <10 μg/L (or <7 μg/L) in response to a standard Provocative Test; and,
(ii.) has a peak serum GH≥5 μg/L in response to a single dose of MK-0677 (e.g., 0.8 mg/kg).

Equivalent growth potential compared to rhGH: a patient is considered to have equivalent growth potential compared to chronic subcutaneous injections of rhGH (equivalent growth potential compared to rhGH) if the patient:
(i.) has a peak serum GH≥5 μg/L in response to a single dose of MK-0677 (e.g., 0.8 mg/kg); and,
(ii.) has a baseline serum IGF-I of >30 μg/L.

Other examples of peak serum GH in response to a single dose of MK-0677 include ≥5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 105, 110, 115, 120 and 125 μg/L.

Low GH secretion potential: a patient is classified as having low GH secretion potential (or severely GH deficient)(LOW) if they show a peak serum GH≤5 μg/L in response to a single oral dose of MK-0677 (0.8 mg/kg).

In another aspect, 0.8 mg/kg/d of MK-0677 is administered. Other examples of the amount of MK-0677 administered include 0.1, 0.2, 0.3, 0.4, 0.5, 0.6, 0.7, 0.9, 1, 1.1, 1.2, 1.3, 1.4, 1.5, 1.6, 1.7, 1.8, 1.9, and 2.0 mg/kg/d and divided doses within this range. Further examples of the amount of MK-0677 administered include at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2.0 mg/kg/d and any divided dose within this range.

In another aspect, in the tests described herein, the single, oral dose of MK-0677 is a single 0.8 mg/kg oral dose. Other examples of the amount of MK-0677 administered for a test include 0.1, 0.2, 0.3, 0.4, 0.5, 0.6, 0.7, 0.9, 1, 1.1, 1.2, 1.3, 1.4, 1.5, 1.6, 1.7, 1.8, 1.9, and 2.0 mg/kg/d and divided doses within this range. Further examples of the amount of MK-0677 administered for a test include at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2.0 mg/kg/d and any divided dose within this range.

In another aspect, MK-0677 is given orally in the form of a mini tablet. In an example, the mini-tablet, comprises: 2 mg of MK-0677. In another example, the mini-tablet, comprises: from 1, 2, 3, 4, 5, 6, 7, 8, 9, 10, 11, 12, 13, 14, 15, 16, 17, 18, 19, to 20 mg of MK-0677. In another example, the mini-tablet, consists essentially of: 2 mg of MK-0677. In another example, the mini-tablet, consists essentially of: from 1, 2, 3, 4, 5, 6, 7, 8, 9, 10, 11, 12, 13, 14, 15, 16, 17, 18, 19, to 20 mg of MK-0677.

The MK-0677 mini-tablet is a small tablet that is capable of being mechanically dispensed (e.g., from a cartridge containing a plurality of tablets). In an aspect, the largest dimension (e.g., height, width, or depth) of the mini-tablet is about 1, 2, 3, 4, to 5 mm. Other examples include a largest dimension of about 2, 3, to 4 mm. In a further example, the largest dimension of the mini-tablet is about 3 mm.

In another aspect, the treatment is maintained for more than 6 months. Other examples include treatment for at least 7, 8, 9, 10, 11, 12, 13, 14, 15, 16, 17, 18, 19, 20, 21, 22, 23, or 24 months. Further examples include treatment for at least 2.5, 3, 3.5, 4, 4.5, 5 years or until growth potential is exhausted.

In another aspect, the child to be treated has never been treated with growth hormone (naïve).

In another aspect, the child to be treated may have received prior GH treatment that is discontinued provided that the child meets the criteria of adequate GH secretion potential as ascertained above.

In another example if the child is shown to be GH deficient when growth is completed, treatment with MK-0677 may be continued to maintain normal GH secretion through adulthood.

In another aspect the level of GH after an acute oral dose of 0.8 mg/kg of MK-0677 is ≥5 µg/mL in radioimmunoassay performed by Endocrine Sciences.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

EXAMPLES

Example 1

Therapeutic Study in Pediatric GH Deficiency: A Phase IIb study was run to determine whether or not MK-0677 could be used to treat pediatric GHD. MK-0677 was compared against placebo and rhGH injections according to the following protocol. Bone age was determined using the atlas matching method of Greulich and Pyle.

Protocol: 6 months of once-daily oral sucrose formulation solution.

Placebo n=22

At 6 months switched to rhGH n=20

MK-0677 (0.4 mg/kg/d) n=22

MK-0677 (0.8 mg/kg/d) n=24

TABLE 1

Results of MK-0677 on the general population of GHD children.

| Delta Height Velocity* | Placebo (n = 22) | GH after placebo 0.3 mg/ kg/week (n = 20) | MK-0677 0.4 mg/ kg/d (n = 22) | MK-0677 0.8 mg/ kg/d (n = 22) | P-value |
|---|---|---|---|---|---|
| Chronological Age (CA) | 0.4 (2.1) | | | | |
| Biological Age (BA) | 0.4 (1.8) | | | | |
| CA | | | 2.6 (1.7) | | 0.0004 |
| CA | | | | 3.5 (2.0) | <.0001 |
| CA | 0.3 (2.2)** | 7.6 (5.6) | | | <0.001 |
| BA | | | 2.6 (1.5) | | <.0001 |
| BA | | | | 3.3 (1.8) | <.0001 |
| BA | 0.2 (1.8)** | 6.2 (3.4) | | | <0.001 |

*Delta height velocity is provided in standard deviations with errors in parentheses.
**For the placebo followed by GH (rhGH), n = 20.

TABLE 2

Characterization of Patients based on growth hormone secretion in response to acute dose of MK-0677 0.8 mg/kg/day

| | All | Low Potential ≤5 µg/L | High Potential ≥5 µg/L | P value |
|---|---|---|---|---|
| Peak GH to MK-0677 | | | | |
| Number of Subjects | 73 | 24 | 49 | |
| Peak GH to MK-0677 | 32 ± 3.5 | 3.0 ± 1.0 | 43 ± 30 | ≤0.0001 |
| Peak GH to Prov. test | 5.3 ± 3.5 | 1.9 ± 1.4 | 6.7 ± 2.4 | ≤0.0001 |
| Baseline IGF-I µg/L | 73 ± 59 | 25 ± 13 | 96 ± 59 | ≤0.0001 |

Peak GH to MK-0677: peak growth hormone to MK-0677 is determined by administering a single dosage of MK-0677 (0.8 mg/kg) and then measuring the peak GH resulting from the MK-0677 dosage.
Low Potential: low GH secretion potential (excluded from present invention).
High Potential: adequate GH secretion potential (included in present invention).
Prov. Test: provocative test.
Baseline IGF-I (Insulin-like Growth Factor): Can be determined by serum measurement e.g by immunoassay or liquid chromatography mass spectroscopy.

Table 3A shows the baseline characteristics of patients with low GH secretion potential (Peak GH to MK-0677≤5 µg/L) who were treated with either MK-0677 (0.8 mg/kg/d) or placebo/rhGH 0.3 mg/kg/week (5 of the 24 children who received placebo for 6 months and then switched to rhGH had low GH secretion potential). Based on height velocity SD for CA, the patients treated with MK-0677 (0.8 mg/kg/day) had more growth retardation than the placebo/GH treated group. However when corrected for bone age they were similar.

TABLE 3A

Baseline data on children with Low GH Secretion Potential (Peak GH to MK-0677 ≤5 µg/L) subsequently treated with MK-0677 or Placebo followed by rhGH

| Baseline | MK-0677 (0.8 mg/kg/d) (N = 9) | Placebo (N = 5) | P-value |
|---|---|---|---|
| Chronological Age | 8.9 (1.8) | 8.9 (4.2) | 0.968 |
| Peak GH response to MK-0677 | 3.2 (1.3) | 2.9 (0.6) | 0.894* |
| Peak GH response to provocative test | 2.4 (2.2) | 1.7 (0.7) | 0.840* |
| Delay in bone age (DBA/CA) | −2.5 (1.8) | −5.0 (3.6) | 0.105 |
| IGF-I | 26.9 (12.4) | 20.4 (12.3) | 0.366 |
| IGF-I SD for chronologic age (CA) | −5.6 (1.6) | −6.8 (2.9) | 0.323 |
| IGF-I SD for bone age (BA) | −4.1 (1.6) | −3.6 (1.2) | 0.529 |

TABLE 3A-continued

Baseline data on children with Low GH Secretion Potential
(Peak GH to MK-0677 ≤5 μg/L) subsequently treated
with MK-0677 or Placebo followed by rhGH

| Baseline | MK-0677 (0.8 mg/kg/d) (N = 9) | Placebo (N = 5) | P-value |
|---|---|---|---|
| Height velocity (HV) | 3.2 (0.9) | 4.5 (1.9) | 0.102 |
| Height velocity SD for CA | −2.8 (1.1) | −0.8 (1.8) | 0.020 |
| Height velocity SD for BA | −3.1 (0.9) | −2.4 (1.2) | 0.261 |

*Denotes non-parametric test.

Table 3B shows that for patients with low GH secretion potential, response to GH injections is superior than response to orally administered MK-0677.

TABLE 3B

Response to MK-0677 versus GH for Patients
with Low GH Secretion Potential

| | MK-0677 (0.8 mg/kg/d) (N = 9) | GH (0.3 mg/kg/wk) (N = 5) | P-value |
|---|---|---|---|
| Height velocity SD for CA* | 2.9 (2.5) | 15.1 (5.1) | 0.001 |
| Height velocity SD for BA* | 2.6 (2.4) | 10.0 (2.2) | 0.002 |
| Delta height velocity (cm/year) | 2.3 (2.0) | 12.3 (4.4) | 0.0878 |

*Tests done on log-scale due to heterogeneity of variance.

Table 4A shows the baseline characteristics of patients with adequate GH secretion potential (Peak GH to MK-0677≥5 μg/L) who were treated with either MK-0677 (0.8 mg/kg/d) or placebo/rhGH 0.3 mg/kg/week (15 of the 24 children who received placebo for 6 months and then switched to rhGH had adequate GH secretion potential.

TABLE 4A

Baseline data on children with Adequate GH Secretion
Potential (Peak GH to MK-0677 ≥5 μg/L) subsequently
treated with MK-0677 or Placebo followed by rhGH.

| Baseline | MK-0677 (0.8 mg/kg/d) (N = 15) | Placebo (N = 15) | P-value |
|---|---|---|---|
| Chronological Age | 8.5 (2.1) | 8.2 (2.4) | 0.739 |
| Peak GH response to MK-0677 | 41.3 (27.8) | 39.2 (28.8) | 0.852* |
| Peak GH response to provocative test | 6.6 (2.4) | 6.9 (2.1) | 0.779 |
| Delay in bone age (DBA/CA) | −2.0 (1.3) | −1.9 (1.2) | 0.925 |
| IGF-I | 101.9 (55.9) | 76.9 (48.0) | 0.199 |
| IGF-I SD for chronologic age (CA) | −1.8 (1.8) | −2.6 (2.2) | 0.264 |
| IGF-I SD for bone age (BA) | −1.0 (1.5) | −1.8 (1.6) | 0.183 |
| Height velocity (HV) | 4.2 (0.8) | 4.4 (1.5) | 0.809 |
| Height velocity SD for CA | −1.7 (0.9) | −1.7 (1.5) | 0.915 |
| Height velocity SD for BA | −1.9 (0.8) | −1.9 (1.4) | 0.887 |

*Denotes non-parametric test.

Table 4B shows that for patients with adequate GH secretion potential, response to MK-0677, while being lower versus GH injections is comparable with GH and was not statistically different. This demonstrates that MK-0677 is an effective growth-promoting therapy in those GHD patients with adequate GH secretion potential

TABLE 4B

Growth Response to MK-0677 versus GH for Patients
with Adequate GH Secretion Potential

| | MK-0677 (0.8 mg/kg/d) (N = 15) | GH 0.3 (mg/kg/wk) (N = 15) | P-value |
|---|---|---|---|
| Height velocity SD for CA | 3.8 (1.7) | 5.1 (2.8) | 0.125 |
| Height velocity SD for BA | 3.8 (1.3) | 4.9 (2.6) | 0.151 |
| Delta height velocity (cm/year) | 3.4 (1.4) | 4.9 (2.9) | 0.0878 |

Table 5A shows the baseline characteristics of patients with low growth potential (Peak GH to MK-0677≤5 μg/L) who were treated with either MK-0677 (0.8 mg/kg/d) or placebo/rhGH 0.3 mg/kg/week (9 of the 24 children who received placebo for 6 months and then switched to rhGH had low growth potential).

TABLE 5A

Figure 1:
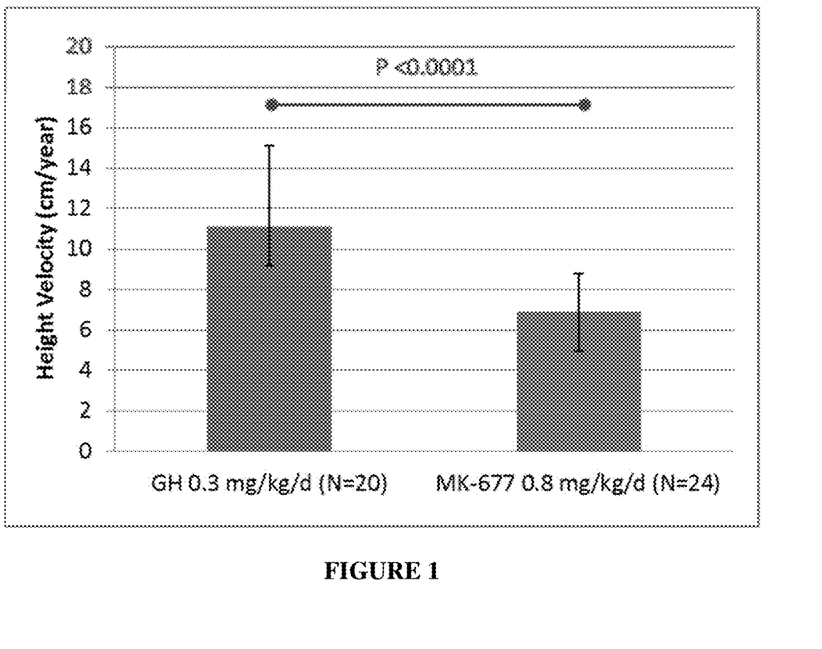
Figure 2:
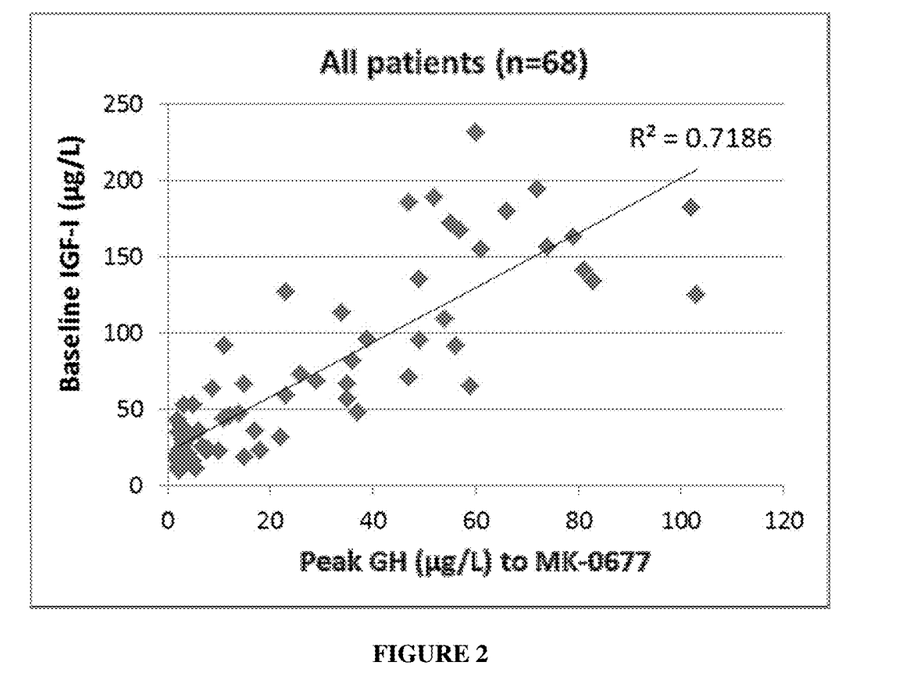
FIG. 2 compares the baseline IGF-I to acute GH response to MK-0677. A tight correlation is seen between baseline IGF-I and acute GH response to MK-0677 ($R^2$=0.7186). Not shown is an observed weak correlation between baseline IGF-I and acute GH response to standard provocative diagnostic tests ($R^2$=0.3316).
Figure 3A:
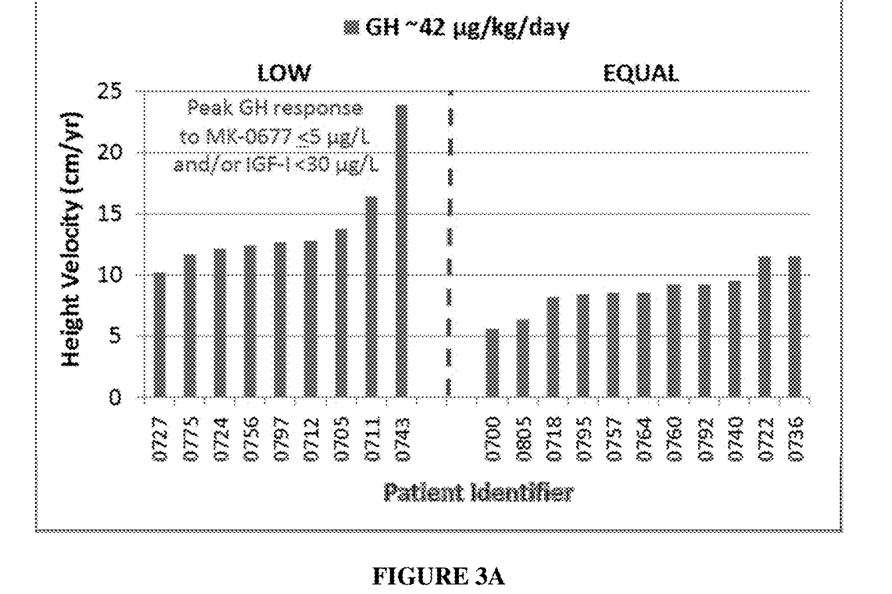
FIGS. 3A and 3B show the height velocity obtained for patients with low growth potential (LOW)(defined below) and equivalent growth potential in response to MK-0677 0.8 mg/k/day compared to rhGH patients (EQUAL) given GH or MK-0677, respectively.
Figure 3B:
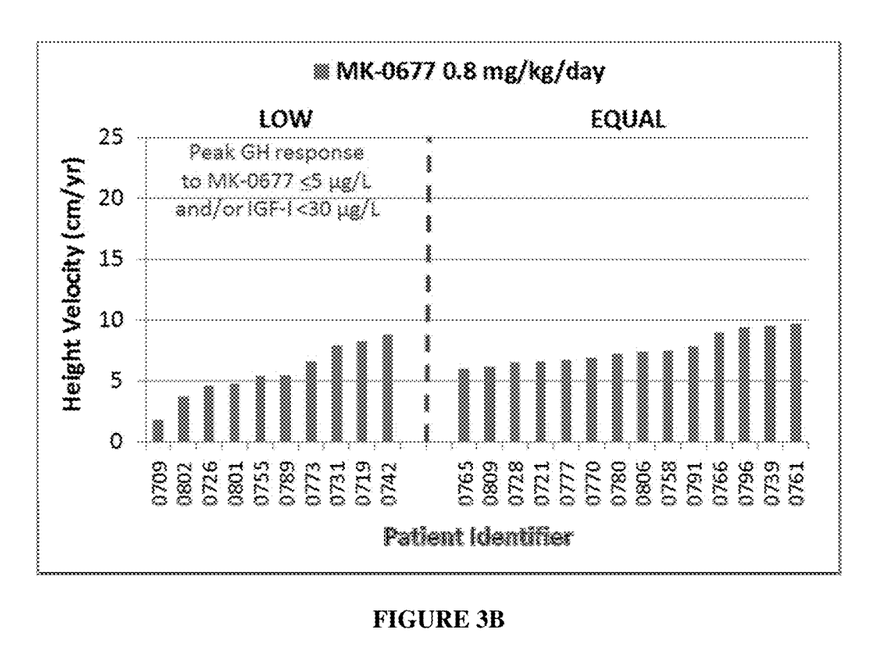
Figure 4A:
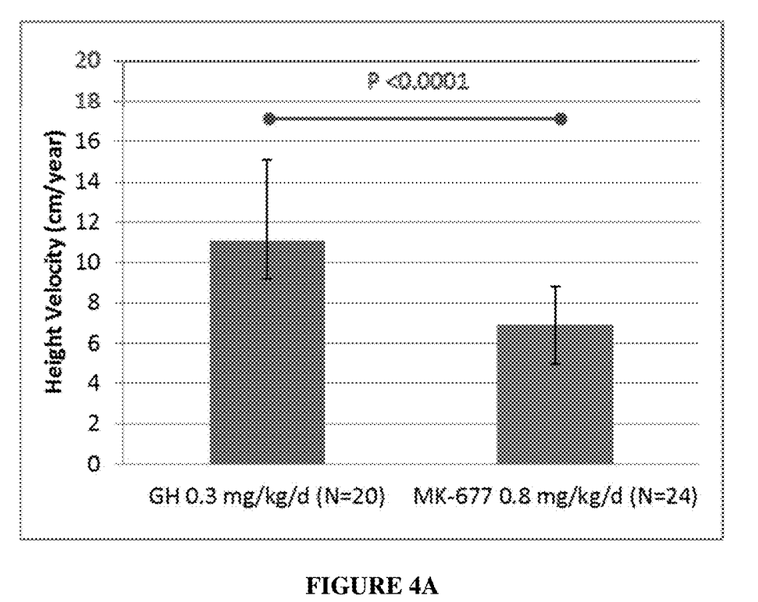
FIGS. 4A and 4B compare the response to GH and MK-0677 in all patients (FIG. 4A) and in EQUAL patients (FIG. 4B). The response to GH in the overall patient group is superior to MK-0677. In contrast, the response to MK-0677 in the EQUAL patient group is equal to GH.
Figure 4B:
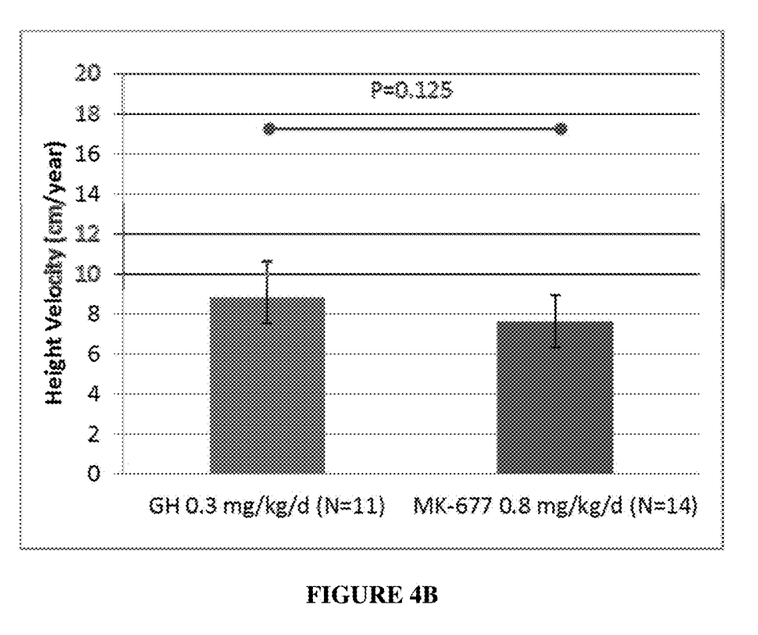
Figure 5A:
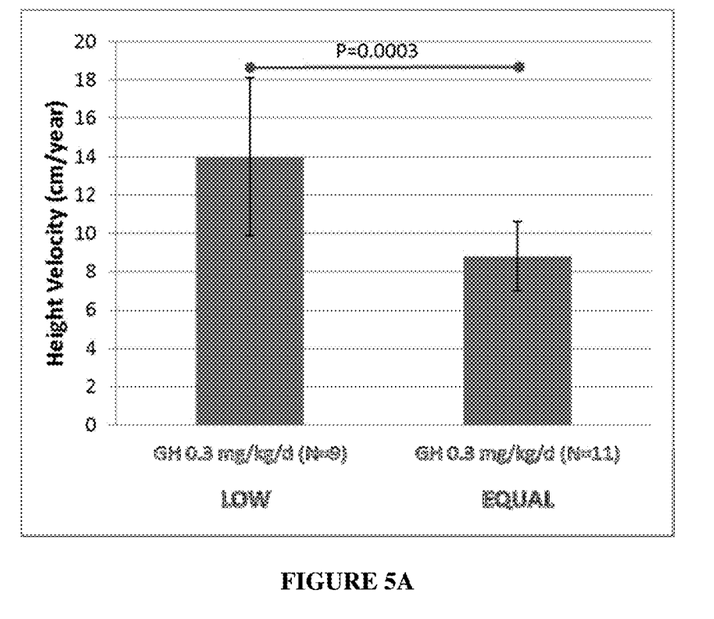
FIGS. 5A and 5B compare the response to GH and MK-0677 in LOW and EQUAL patients. LOW patients are extremely sensitive to GH. EQUAL patients have a smaller response to GH. LOW growth potential patients show an inadequate growth response to MK-0677. In contrast, EQUAL growth potential patients show a growth response to MK-0677 that does not differ significantly from that to GH (P=0.125).
Figure 5B:
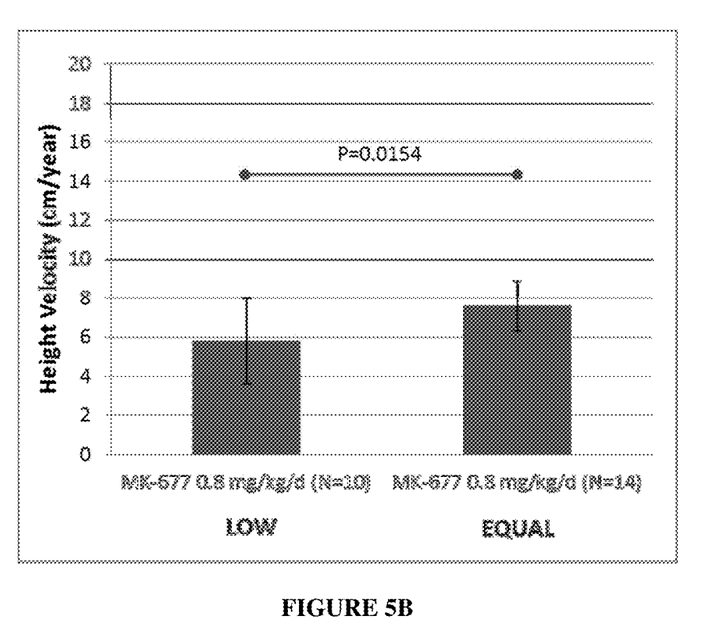

Increased response to GH vs MK-0677 in children
with low potential growth (see FIGS. 5A and 5B)

| Baseline | MK-0677 0.8 mg/kg (N = 10) | Placebo (N = 9) | P-Value |
|---|---|---|---|
| Age | 8.8 (1.8) | 8.3 (3.8) | 0.715 |
| Peak GH response to MK-0677 | 3.6 (1.7) | 6.7 (5.9) | 0.205* |
| Peak GH response provocative/stimulation test | 2.6 (2.1) | 3.2 (2.1) | 0.287* |
| Delay in bone age (DBA/CA) | −2.5 (1.7) | −4.0 (3.0) | 0.191 |
| IGF-I | 26.8 (11.7) | 19.9 (9.5) | 0.178 |
| IGF-I SDS for chronologic age (CA) | −5.4 (1.5) | −6.2 (2.5) | 0.44 |
| IGF-I SDS for bone age (BA) | −4.0 (1.6) | −3.7 (1.1) | 0.645 |
| Height velocity (HV) | 3.2 (0.9) | 4.2 (2.1) | 0.188 |
| Height velocity SDS for CA | −2.7 (1.0) | −1.5 (2.1) | 0.123 |
| Height velocity SDS for BA | −3.1 (0.9) | −2.6 (1.4) | 0.413 |

| After 6 months of treatment | MK-677 0.8 mg/kg (N = 10) | GH~42 μg/kg/day (N = 9) | P-value |
|---|---|---|---|
| Height velocity (cm/year) | 5.8 (2.2) | 14.0 (4.1) | 0.0002 |

*Denotes non-parametric test.

Table 5B shows the baseline characteristics of patients with high growth potential (Peak GH to MK-0677≤5 μg/L) who were treated with either MK-0677 (0.8 mg/kg/d) or placebo/rhGH 0.3 mg/kg/week (11 of the 24 children who received placebo for 6 months and then switched to rhGH had high growth potential).

TABLE 5B

Similar growth response to GH and MK-0677 in children
with equivalent growth potential (see FIGS. 5A and 5B)

| Baseline | MK-0677 0.8 mg/kg (N = 14) | Placebo (N = 13) | P-value |
|---|---|---|---|
| Age | 8.6 (2.2) | 8.4 (2.1) | 0.848 |
| Peak GH response to MK-0677 | 43.7 (27.1) | 51.2 (25.3) | 0.465 |
| Peak GH response provocative/stimulation test | 6.9 (2.3) | 7.7 (1.8) | 0.286 |
| Delay in bone age (DBA/CA) | −2.0 (1.3) | −1.8 (0.9) | 0.671 |

TABLE 5B-continued

Similar growth response to GH and MK-0677 in children with equivalent growth potential (see FIGS. 5A and 5B)

| Baseline | MK-0677 0.8 mg/kg (N = 14) | Placebo (N = 13) | P-value |
|---|---|---|---|
| IGF-I | 107.4 (53.8) | 101.7 (42.4) | 0.765 |
| IGF-I SDS for chronologic age (CA) | −1.6 (1.8) | −1.4 (0.9) | 0.781 |
| IGF-I SDS for bone age (BA) | −0.8 (1.4) | −0.9 (0.9) | 0.949 |
| Height velocity (HV) | 4.3 (0.8) | 4.4 (1.0) | 0.452* |
| Height velocity SDS for CA | −1.7 (0.9) | −1.5 (1.0) | 0.597 |
| Height velocity SDS for BA | −1.8 (0.8) | −1.8 (1.1) | 0.862 |

| After 6 months of treatment | MK-677 0.8 mg/kg (N = 14) | GH ~42 µg/kg/day (N = 11) | P-value |
|---|---|---|---|

| After 6 months of treatment | MK-0677 0.8 mg/kg (N = 14) | GH~42 µg/kg/day (N = 11) | P-value |
|---|---|---|---|
| Height velocity (cm/year) | 7.6 (1.3) | 8.8 (1.8) | 0.125 |

*Denotes non-parametric test.

Tables 6A-6E show the height velocity for EQUAL growth potential children treated with either 0.8 mg/kg/daily po or 0.4 mg/kg/daily po MK-0677 compared with rhGH (0.3 mg/kg/week; ~42 µg/kg/daily sc injection). LOW growth potential patients are those that do not satisfy the equivalent growth potential compared to rhGH (EQUAL) test described previously. Values are mean (SD).

TABLE 6A

Height Velocity LOW and EQUAL Combined, 6-Month MK 0.8 mg/kg/day vs. 6-Month GH (0.3 mg/kg/week)

| | MK-677 0.8 mg/kg (N = 24) | GH (N = 20) | P-value |
|---|---|---|---|
| Height Velocity | 6.9 (1.9) | 11.1 (4.0) | <.0001 |

TABLE 6B

Height Velocity LOW and EQUAL Combined, 6-Month MK 0.8 mg/kg/day Vs. 6-Month Placebo

| | MK-677 0.8 mg/kg (N = 24) | Placebo (N = 22) | P-value |
|---|---|---|---|
| Height Velocity | 6.9 (1.9) | 4.5 (1.4) | <.0001 |

TABLE 6C

Height Velocity LOW and EQUAL Combined, 6-Month MK 0.4 mg/kg/day Vs. 6-Month Placebo

| | MK-677 0.4 mg/kg (N = 22) | Placebo (N = 22) | P-value |
|---|---|---|---|
| Height Velocity | 6.0 (1.9) | 4.5 (1.4) | 0.0046 |

TABLE 6D

Height Velocity LOW and EQUAL Combined, 6-Month MK 0.4 mg/kg/day Vs. 6-Month MK 0.8 mg/kg/day

| | MK-677 0.4 mg/kg (N = 22) | MK-677 0.8 mg/kg (N = 24) | P-value |
|---|---|---|---|
| Height Velocity | 6.0 (1.9) | 6.9 (1.9) | 0.1325 |

TABLE 6E

Height Velocity LOW and EQUAL Combined, Paired T-test 6-Month Placebo vs. 6-Month GH (20 of the 22 children were switched to rhGH after 6 months for a further 6 months).

| | Placebo (6-Month) | GH (12-Month) | P-Value |
|---|---|---|---|
| Height Velocity | 4.48 (1.44) (N = 22) | 11.14 (3.96) (N = 20) | <.0001 |

Tables 7A-7C compare the height velocity for low growth potential patients (LOW) with equivalent growth potential compared to rhGH (EQUAL). Values are mean (SD).

TABLE 7A

Height Velocity EQUAL vs. LOW, 6-Month MK 0.4 mg/kg/day

| | EQUAL (N = 12) | LOW (N = 10) | P-value |
|---|---|---|---|
| Height Velocity | 6.2 (1.8) | 5.8 (2.1) | 0.6923* |

*Denotes non-parametric test was used.

TABLE 7B

Height Velocity EQUAL vs. LOW, 6-Month MK 0.8 mg/kg/day

| | EQUAL (N = 14) | LOW (N = 10) | P-value |
|---|---|---|---|
| Height Velocity | 7.6 (1.3) | 5.8 (2.2) | 0.0154 |

TABLE 7C

Height Velocity EQUAL vs. LOW, 6-Month rhGH

| | EQUAL (N = 11) | LOW (N = 9) | P-value |
|---|---|---|---|
| Height Velocity | 8.8 (1.8) | 14.0 (4.1) | 0.0003* |

*Denotes non-parametric test was used.

Note that with MK-0677 the height velocity in the LOW group is lower than with the EQUAL group. In contrast the height velocity with GH is greater in the LOW group than in the EQUAL group (see FIGS. 5A and 5B). This is explained by greater sensitivity to GH replacement in severely GH deficient children in the rhGH treated children. In the 0.8 mg/kg/day po MK-0677 treated children the LOW growth potential children are unable to secrete enough endogenous GH to sustain the same height velocity compared to exogenous rhGH injections while in the EQUAL growth potential patients they are able to secrete enough endogenous GH to produce the same growth response as to daily exogenous rhGH injections.

Example 2

| Dosages of MK-0677 For Growth Hormone Deficient Children | | |
|---|---|---|
| Subject's Weight | MK-0677 Dose 0.8 mg/kg/day | Number of 2-mg Mini-tablets |
| 15 kilograms to <20 kilograms | 12 mg | 6 |
| 20 kilograms to <25 kilograms | 16 mg | 8 |
| 25 kilograms to <30 kilograms | 20 mg | 10 |
| 30 kilograms to <35 kilograms | 24 mg | 12 |
| 35 kilograms to <40 kilograms | 28 mg | 14 |
| 40 kilograms to <45 kilograms | 32 mg | 16 |
| >45 kilograms | 36 mg | 18 |

Example 3

Identification of Growth Hormone Deficient Children Who Will have an Equal Increase in Growth Velocity to Once Daily Oral MK-0677 Therapy Equally as they Would to Daily Subcutaneous Recombinant Injections.

Baseline Serum IGF-1 Versus Peak Response to MK-0677 (0.8 mg/kg) Po:

For each IGF1 (30 to 100 by 10) cutpoint used to define "truth", in the table below the area under the ROC curve and the cutpoints for responses to the Theranostic test with MK-0677 (0.8 mg/kg orally) on each criteria.

(i.) The distance from each point on the ROC curve to the upper left hand corner of the plotting area (sensitivity=1 and 1−specificity=0). The cutpoint is the value associated with the minimum distance from the curve to this point.

(ii.) The second gives equal weight to sensitivity and specificity and calculates the absolute difference between the two. The cutpoint is the value associated with the minimum difference between sensitivity and specificity.

(iii.) The third calculated the distance from the uninformative diagonal line on a curve to each point. The cutpoint is value that maximizes this distance. This is Youden's statistic.

The rank ordering of the IGF1 and peak GH stimulated by MK-0677 are very similar, with a Spearman correlation of 0.82.

| | | Cutpoint Based on MK-0677 stimulated GH peak Cutpoint Selection Criterion | | |
|---|---|---|---|---|
| IGF1 µg/L Cutpoint | Area Under ROC Curve | Minimum Distance from ROC point to sensitivity = 1, 1−specificity = 0 plot point (upper left corner of the ROC curve) | Minimum of Absolute Difference of Sensitivity Minus Specificity | Maximum Youden index (the vertical distance from the uninformative diagonal to the cutpoint) |
| 30 | 0.8535 | 7.5 | 6.9 | 22 |
| 40 | 0.9251 | 15 | 14 | 23 |
| 50 | 0.9806 | 17 | 17 | 23 |
| 60 | 0.9517 | 23 | 22 | 23 |
| 70 | 0.9351 | 23 | 29 | 23 |
| 80 | 0.9186 | 26 | 35 | 23 |
| 90 | 0.9272 | 36 | 36, 37 | 36 |
| 100 | 0.9232 | 47 | 47 | 36 |

Standard Stimulation Test Results and Results from Theranostic Test with MK-0677 (0.8 g/kg) in Growth Hormone Deficient Children:

3 different criteria for determining the best cutpoint from each ROC curve (i.) The distance from each point on the ROC curve to the upper left hand corner of the plotting area (sensitivity=1 and 1−specificity=0). The cutpoint is the value associated with the minimum distance from the curve to this point.

(ii.) The second gives equal weight to sensitivity and specificity and calculates the absolute difference between the two. The cutpoint is the value associated with the minimum difference between sensitivity and specificity.

(iii.) The third calculated the distance from the uninformative diagonal line on a curve to each point. The cutpoint is value that maximizes this distance. This is Youden's statistic.

GH cutpoint of 3 µg/L, use a MK-0677 cutpoint of 7 µg/L
GH cutpoint of 4 µg/L, use a MK-0677 cutpoint of 12 µg/L
GH cutpoint of 5 or 6 µg/L, use a MK-0677 cutpoint of 17 µg/L
GH cutpoint of 7 or 8 µg/L, use a MK-0677 cutpoint of 35 µg/L

| | | Cutpoint Based on MK-0677MK-0677 Stimulated peak GH Cutpoint Selection Criterion | | |
|---|---|---|---|---|
| Peak GH µg/L Stimulation Cutpoint | Area Under ROC Curve | Minimum Distance from ROC point to sensitivity = 1, 1−specificity = 0 plot point (upper left corner of the ROC curve) | Minimum of Absolute Difference of Sensitivity Minus Specificity | Maximum Youden index (the vertical distance from the uninformative diagonal to the cutpoint) |
| 3 | 0.9706 | 6.9 | 7.5 | 6.9 |
| 4 | 0.9777 | 12 | 11 | 12 |
| 5 | 0.9363 | 17 | 15 | 22 |
| 6 | 0.9335 | 17 | 17 | 12, 15, 17, 22 |
| 7 | 0.8932 | 34 | 29 | 15 |
| 8 | 0.8240 | 35 | 36 | 17 |
| 9 | 0.8078 | 36 | 37 | 22 |
| 10 | 0.8958 | 56 | 56 | 56 |

Based on the above data, the following segregation of patients can be made.

(i.) Low Growth Potential: When growth hormone deficient children were segregated based on their baseline serum IGF-1 of <30 µg/L and/or their response the Theranostic test with a serum GH of <5 µg/L to a single dose of 0.8 mg/kg oral MK-0677, they were considered to have low growth potential to MK-0677 but high growth potential to recombinant human growth hormone.

(ii.) Equivalent Growth Potential: However if their baseline serum IGF-1 was >30 µg/L and their peak serum GH of ≥5 µg/L to a single dose of 0.8 mg/kg oral MK-0677 they are considered to have equivalent (EQUAL) growth potential to oral MK-0677 (0.8 mg/kg/day) as to injections sc of recombinant human growth hormone daily.

Example 4

Theranostic MK-0677 Test:

Subjects will report to the clinic in the morning after an overnight fast from all food and drink except water. A catheter will be inserted approximately 1 hour before the administration of MK 0677. Two baseline measures will be taken a t=−15 minutes and t=0 minutes (time at which subject is administered the dose). Subjects will be given a dose of 0.8 mg/kg MK-0677 as 2-mg tablets to be taken orally. Blood samples will be taken subsequently at t=30, 60, 90, 120 minutes. In addition at t=−15 and 120 minutes, samples will be drawn for a serum chemistry panel. At the conclusion of the test, the catheter will be removed. All blood samples will be analyzed for GH, prolactin, and cortisol by a core clinical laboratory.

No data are available on the combination of an MK-0677 response test with a standard GH provocative test. For this reason, the MK-0677 provocative test should be separated from other provocative tests by at least 3 days.

Standard Growth Hormone Provocative Tests

In addition to the Theranostic MK-0677 test, the patient should also be subjected to a provocative GH test. These tests include the known Clonidine Test, Insulin Test, Arginine Test, Glucagon Test, and Levodop (L-dopa) test. Examples of test protocols for these tests are provided below.

Clonidine Test

A catheter will be inserted at least 1 hour prior to the administration of clonidine. Two baseline blood samples should be obtained, one at t=−15 minutes and another immediately preceding the clonidine dose. Clonidine will be given orally to the patient in tablet form. Patients weighing 20 to 35 kilograms will receive a dose of 100 micrograms. Patients exceeding 35 kilograms will receive a dose of 200 micrograms. Subsequent blood samples will be taken at t=30, 60, 90, and 120 minutes. Blood pressure will be monitored after each blood sample.

The risks associated with clonidine testing include possible hypotensive side effects and somnolence.

Insulin Test

A catheter should be inserted at least 1 hour prior to the administration of insulin. Two baseline blood samples should be obtained, one at t=−15 minutes and another immediately preceding the insulin dose. One-tenth unit kilograms of insulin will be injected. Blood samples should be taken at t=15, 30, 45, 60, 90, and 120 minutes.

Insulin testing will only be considered successful if the blood sugar level decreases to at least half of its fasting value. Possible risks of this test include palpitations, tremors, severe hypoglycemia, seizures, and in some instances, death. Glucose and glucagon should be prepared and be available for injection in the event of an emergency. An experienced physician should be at the bedside throughout the test to monitor for side effects. At the conclusion of the test, patient should be given a meal immediately.

Arginine Test

A catheter and an IV should be inserted 1 hour prior to the administration of arginine. Two baseline blood samples should be taken, one at t=−15 minutes and another just prior to the arginine injection. Arginine should be given at a dose of 0.5 g/kg with a maximum dose not to exceed 30 g. The intravenous injection of arginine should be administered continuously throughout the first 30 minutes of the test. Subsequent blood samples should be drawn at t=30, 60, 90, and 120 minutes.

There are no severe risks associated with this test. Possible side effects include flushed appearance, nausea, vomiting, numbness, headaches, and local venous irritation.

Glucagon Test

A catheter should be inserted at least 1 hour prior to the administration of glucagon. Baseline blood samples should be drawn at t=−15 minutes and immediately preceding the injection. Glucagon will be given as an intramuscular injection at a dose of 1 mL for patients weighing 10 to 35 kilograms. Subsequent blood samples should be drawn at t=30, 60, 90, 120, and 150 minutes.

There are no severe risks associated with this test. In some patients, nausea and vomiting may occur.

Levodopa (L-Dopa) Test

A catheter will be inserted at least 1 hour prior to the administration of L-dopa. Blood samples should be drawn at t=−30 and −15 minutes and immediately prior to dosage. Two-hundred and fifty milligrams of L-dopa will be administered in tablet form to patients weighing 15 to 30 kilograms and 500 milligrams of L-dopa will be administered orally in tablet form to patients weighing more than 30 kilograms. Subsequent blood samples will be drawn at t=30, 60, 90, and 120 minutes.

There are no severe risks associated with this test. Possible side effects include nausea, vomiting, and headaches.

Numerous modifications and variations of the present invention are possible in light of the above teachings. It is therefore to be understood that within the scope of the appended claims, the invention may be practiced otherwise that as specifically described herein.

What is claimed is:

1. A method of treating growth hormone deficiency (GHD) in children, comprising: administering a therapeutically effective amount of MK-0677 to a child known to have short stature and equivalent growth potential compared to rhGH, wherein a child has equivalent growth potential compared to rhGH when the child has:
   (i.) a peak serum GH ≥5 μg/L in response to a single oral dose of MK-0677; and,
   (ii.) a baseline serum IGF-I of >30 ng/mL.

2. The method of claim 1, wherein a single, oral 0.8 mg/kg/d dose of MK-0677 is administered.

3. The method of claim 1, wherein MK-0677 is orally administered via at least one mini-tablet, comprising: MK-0677.

4. The method of claim 3, wherein the mini-tablet, comprises: 2 mg of MK-0677.

5. The method of claim 1, wherein the GHD is pediatric GHD.

6. The method of claim 1, wherein MK-0677 is orally administered and the orally administering, further comprises: administering with the assistance of a device capable of dispensing at least one MK-0677 mini-tablet.

7. A method of treating GHD in children, comprising:
   a testing a child known to have short stature for GHD using a theranostic test; and,
   b orally administering a therapeutically effective amount of MK-0677 to a child found to have short stature and equivalent growth potential compared to rhGH;
wherein a child has equivalent growth potential compared to rhGH when the child has:
   (i.) a peak serum GH ≥5 μgL in response to a single oral dose of MK-0677; and,
   (ii.) a baseline serum IGF-I of >30 ng/mL.

8. The method of claim 7, wherein a single, oral 0.8 mg/kg/d dose of MK-0677 is administered.

9. The method of claim 7, wherein MK-0677 is orally administered via at least one mini-tablet, comprising: MK-0677.

10. The method of claim 9, wherein the mini-tablet, comprises: 2 mg of MK-0677.

11. The method of claim 7, wherein the orally administering, further comprises: administering with the assistance of a device capable of dispensing at least one MK-0677 mini-tablet.

12. The method of claim 7, wherein the GHD is pediatric GHD.

13. The method of claim 7, wherein the theranostic test, comprises:
- (iii.) testing for a peak serum GH $\geq 5$ μg/L in response to a single oral dose of MK-0677; and,
- (iv.) testing for a baseline serum IGF-I of >30 ng/mL.

14. The method of claim 13, wherein a single, oral 0.8 mg/kg/d dose of MK-0677 is administered in step (i).

15. The method of claim 1, wherein the treatment is maintained for more than 6 months.

16. The method of claim 1, wherein the treatment is maintained for at least 7 months.

17. The method of claim 1, wherein the treatment is maintained until growth potential is exhausted.

18. The method of claim 7, wherein the treatment is maintained for more than 6 months.

19. The method of claim 7, wherein the treatment is maintained for at least 7 months.

20. The method of claim 7, wherein the treatment is maintained until growth potential is exhausted.

* * * * *